United States Patent [19]

Ascher et al.

[11] Patent Number: 4,643,893
[45] Date of Patent: Feb. 17, 1987

[54] PROGRAMMED RELEASE DEVICE AND METHOD OF USE THEREOF

[75] Inventors: Frédéric M. Ascher, Carros; Jacques A. Cuvelier, St. Martin du Var, both of France

[73] Assignee: C.R.B. Virbac S.A., Carros, France

[21] Appl. No.: 708,877

[22] Filed: Mar. 6, 1985

[30] Foreign Application Priority Data

Mar. 7, 1984 [FR] France .................. 84 03520

[51] Int. Cl.$^4$ .................. A61K 9/70; A61J 3/00
[52] U.S. Cl. .................. 424/16; 424/19;
424/20; 424/21; 424/22; 424/33
[58] Field of Search .................. 424/15, 16, 18, 19,
424/20, 21, 22, 32, 33; 604/49

[56] References Cited

U.S. PATENT DOCUMENTS 4,012,497 3/1977 Schopflin .................. 424/15
4,308,250 12/1981 Griffin et al. .................. 424/16
4,405,360 9/1983 Cardarelli .................. 71/117
4,505,711 3/1985 Lucas .................. 424/19

FOREIGN PATENT DOCUMENTS 2370949 6/1978 France .
2393576 1/1979 France .

Primary Examiner—John Kight
Assistant Examiner—Nathan M. Nutter
Attorney, Agent, or Firm—Berman, Aisenberg & Platt

[57] ABSTRACT

There is disclosed a novel device intended to permit the regular and continuous release of chemical substances, including medicaments, and this, over a very long period of time, the release of the active substances following a predetermined kinetic effect from an insoluble polymeric matrix to a liquid medium which can be, particularly, that of an animal or human organism. The device has a specific density to remain in an animal rumen. There is also disclosed a method for treating animals by means of such devices.

19 Claims, 6 Drawing Figures

U.S. Patent   Feb. 17, 1987   4,643,893
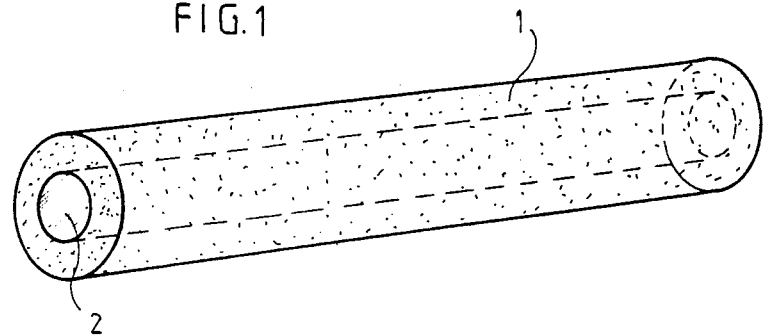
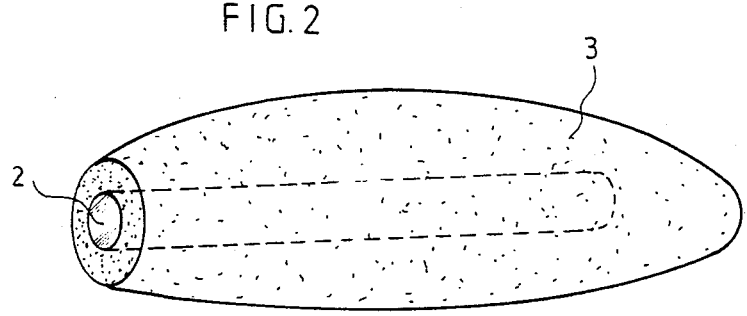
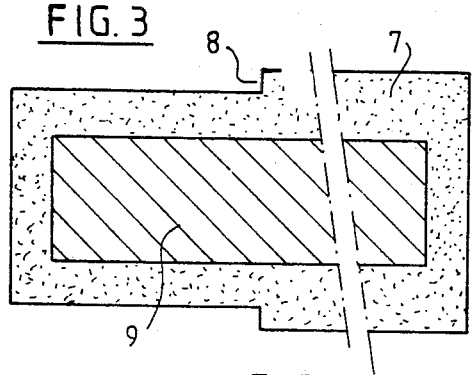
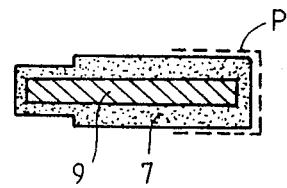
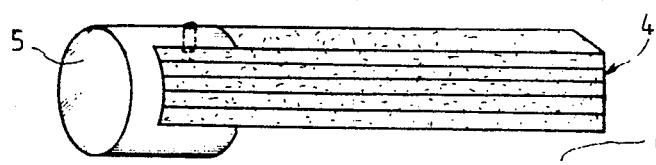
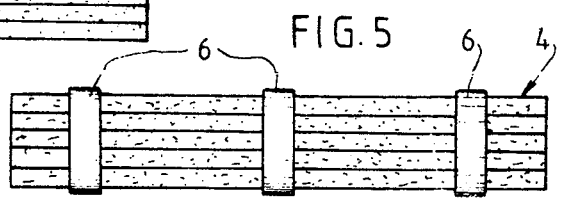

PROGRAMMED RELEASE DEVICE AND METHOD OF USE THEREOF

BACKGROUND OF THE INVENTION

The present invention relates to a novel device intended to permit the regular and continuous release of chemical substances, meaning also medicaments, and this, over a very long period, the release of the active substances following a predetermined kinetic effect from an insoluble polymeric matrix to a liquid medium which can be, particularly, that of an animal or human organism.

Very many systems are known which permit the regulated and programmed release of pharmaceutically-active substances.

These are all solid or semi-solid systems, of the type, for example, of tablets or suppositories whose composition is defined so as to result in a slow disintegration of the system, the disintegration itself being produced, either by a purely mechanical effect or by partial solubilization by the liquid medium, for example, body fluids of one or several components forming the system.

It is also known to disperse the active principle in a solid support and to produce its programmed release by diffusion through such a support.

In this case also, the systems described are numerous: so-called semi-permeable systems are known in which the active agent (dissolved, suspended or emulsified in an inert vehicle) diffuses through a permeable membrane;

composite systems are also known in which the active agent diffuses from a more or less porous solid support, constituted by a matrix based on polymers or copolymers.

Whatever the system selected, the speeds of release are only maintained over a very short period of time and hence do not lend themselves to prolonged use.

In particular, in the veterinary field, the repeated administration of medicinal substances runs up against both economic and technical problems when animals, for example, are very numerous or dispersed in pastures.

Also, various devices have been designed so as to permit activity over a prolonged period, and, in particular, as medicinal release systems in ruminants.

Thus, there have been described, for example:

a medicament with a prolonged delayed reaction characterized in that it is in the form of a parallelepipedic article about 7 to 8 cm long and weighing about 10 to 60 g (Fr. P. 2 461 495). However, the life span of such a device hardly exceeds some days;

a device designed for continuous and regulated administration of a chemical substance, characterized in that it is formed from a reservoir of heavy material, for example, a metal cylinder provided at one of its ends with a porous wall (for example a semi-permeable membrane) through which said chemical substance diffuses (cf. French Pat. No. 2 425 242). Such a device, even if it completely fulfils the role of a longterm diffuser (two to three months), has however two important drawbacks:

the diffusion surface is very small, resulting in a low and insufficient concentration of active substances on the one hand and frequent clogging on the other hand.

GENERAL DESCRIPTION OF THE INVENTION

Accordingly, it is an object of the present invention to provide a device enabling the release at a regulated speed into a liquid medium of one or more substances active in veterinary medicine, said device being constituted by a macromolecular thermoplastic solid matrix support (based on insoluble polymers or copolymers associated with adjuvants and additives) enabling the progressive and programmed release of one or more active substances incorporated therein, characterized in that the initial concentration of the one or more active substances, on the one hand, and the surface of the device through which the diffusion is effected, on the other hand, are determined as a function of the period of release and the amount desired to be released daily, the matrix support containing the one or more active substances and totally or almost totally enclosing one or more masses of dense material, conferring to the whole device a density higher than 1.3 g/ml.

The devices according to the present invention enable the diffusion of active substances at a constant and uniform speed throughout the life of the device, that is to say until complete or almost complete diffusion of the active substance.

The device according to the present invention may be used as a diffuser of medicinal substances in humans or in animals. It may be used for the prevention or treatment of disorders of animal organisms, namely: through individual administration; the device being introduced in the form of a bolus into the animal organism or by collective administration, wherein the device is introduced into a liquid medium used by animals, for example, aquaria, fish ponds, hydroponic installations, water distributing systems for animals, etc.

The present invention relates more particularly to devices enabling the diffusion of active substances in a form permitting oral administration to animals and especially to ruminants, these devices being introduced into the rumino-reticular bag where they are retained for a very long period, and this by reason of their specific gravity, higher than that of the liquid in which they are immersed.

In an advantageous embodiment of the invention, the device is in cylindrical or oblong form.

According to another embodiment of the invention the device is constituted by a plurality of superposed strips surrounded, possibly, by a biodegradable jacket of cylindrical or oblong shape.

According to the invention, the dense material is housed inside the matrix support.

According to another feature of the invention, the dense material is in the form of rings and/or shapes surrounding the matrix support. Thus, the device according to the invention, whatever the modification produced—dense mass inside the cylinder or ring of small surface area surrounding the matrix support—, enables regular diffusion and in constant proportions throughout the life of the device.

In accordance with the invention, the matrix support is produced by extrusion or hot molding of polymers or copolymers of chemical substances taken from the group which comprises vinyl polymers, polyethylenes, polypropylenes, polyacetates, polyurethanes, and vinyl acetates.

The matrix support comprises, also, various additives, such as placticizers (selected from the esters: cresyl phthalates, adipates, sebacates or phosphates), stabilizers, and lubricants, permitting molding or extrusion of the devices.

According to one embodiment of the present invention, it is advantageous to include in the matrix support, inert substances enabling the precise and continuous regulation of the release of the active principle. Among these soluble substances, may be mentioned, by way of example, sugars (lactose, saccharose, glucose), starches, soluble celluloses, gelatins.

In an advantageous embodiment of the invention, the dense materials are selected among minerals and/or metals. Thus all the devices of cylindrical or oblong shape are produced so as to form an internal cavity which can be filled by the dense element, for example, metal. In this manner, the initial shape retained is not affected by the operation of making the device heavier.

It is also possible, from solid polymer matrixes, to fix a metal weight, either at one or both ends, or again metal rings positioned at regular intervals.

In the case where the matrix is in the form of several strips, the latter are held, for example, at one of their ends by a dense metal tip, the whole being held in a hydrolysable jacket in the animal system (cellulose or gelatin for example).

The choice of the one or more active substances incorporated in the polymeric matrix depends upon the desired purpose.

It may be therapeutic or prophylactic in the case of human or veterinary medicine.

In this respect, the invention also relates to a method of treating ruminants by means of a device, such as described above, said device being in the form of a bolus whose regurgitation is prevented so that all or almost all of the active substance is absorbed according to a predetermined time program.

The purpose may be industrial and addressed, in particular, to the agricultural domain for the delivery of pesticidal substances.

The active substances can hence include medicinal substances useful in humans and animals or inorganic chemical substances. Thus, recourse may be had to substances with antiparasitic, antihelmintic antibiotic, antifungal, antibacterial, anticoccidial activity, to substances used as a growth factor, to inorganic nutrient agents or vitamin nutrient agents. Substances with pesticidal activity may also be resorted to.

The novel systems, with programmed release, as defined in the present invention, can permit the release of chemical substances including medicaments when they are used in media which contain liquids. They are, in particular, well adapted to the release of both very water-soluble and slightly water-soluble chemical substances.

The release is constant, continuous, and this, over a very long period.

In their design, the devices according to the invention are easy to produce and prove to be of a form particularly well adapted for oral administration in ruminants.

The diffusion of the active substances, is effected through the whole surface of the devices, no risk of clogging or of modification of the elimination is to be feared.

The method of preparing devices according to the present invention is that of thermoplastic substances which can be worked, either by molding, or by hot extrusion.

The choice of technique is conditioned by the form of the devices to be produced.

The production of a strip or of a hollow cylinder is done by extrusion. One or more metal parts, serving as a ballast, are added in the course of a second step.

The various forms used: cylindrical, ovoid, oblong, are obtained by hot molding. In this case, the matrix support is molded directly around the central metal part, the device being obtained in as single step.

In a particularly advantageous modality of the device according to the invention, said device is enveloped in a sheath of biodegradable material, in order to facilitate the oral administration thereof in animals.

In a particular embodiment of the devices, it is contemplated the partial covering of the outer surface of the matrix support by an impermeable film, and this for the purpose of reducing the daily amount of active principle and increasing further the effective life of the device.

The film deposit may be effected with any impermeable substance, but polymerizable products, such as cross-linkable silicone elastomers and epoxy resins, are preferred for their ease of application.

Besides the foregoing features, the invention comprises also other features which will emerge from the description which follows, reference being made to embodiments of the devices according to the present invention shown in the accompanying drawings, to examples of the composition of the matrix supports, including additives and medicaments as well as to reports of experiments on animals.

BRIEF DESCRIPTION OF THE DRAWINGS

In the drawings:

FIG. 1 is a diagramatic view of an embodiment of the device according to the present invention, FIG. 2 shows a diagramatic view of another embodiment according to the present invention, FIG. 3 shows a diagramatic view (in longitudinal section) of another embodiment of a device according to the invention, FIG. 3a shows a view similar to that of FIG. 3, but for a modification of this embodiment, FIGS. 4 and 5 show diagramatically, further embodiments of the device according to the invention.

It must be well understood, however, that these drawings, examples and reports, as well as the corresponding descriptive portions, are given purely by way of illustration of the invention of which they do not constitute in any way a limitation thereof.

DESCRIPTION OF PREFERRED EMBODIMENTS

The device according to the invention shown in FIG. 1 has the shape of a cylinder, composed of two portions: an outer portion 1 formed from the matrix support comprising additives and active substances and an inner portion 2 formed from a metal core, for example, of stainless steel. It is this metal core which confers on the device the desired overall density without affecting in any way the very large surface of contact and of diffusion which characterizes the devices according to the present invention. In the embodiment shown in FIG. 2 the outer portion 3 (matrix support) has an oblong shape, whilst the inner portion is, as previously, constituted by a stainless steel cylinder.

In the embodiment of the device shown in FIG. 3, the outer portion 7 (matrix support) has a cylindrical shape having a recessed portion 8 on one end and completely surrounds the inner portion 9 which is, as previously, constituted by a metal cylinder. The same remark applies to the modification shown in FIG. 3a, where P represents a fine film of silicone elastomer cross-linkable at normal temperature of 5/10 mm thickness.

In the embodiment shown in FIGS. 4 and 5 the matrix is in the form of five strips 4 held at one of their ends by a tip of stainless steel 5 (FIG. 4) or, for example, three regularly spaced stainless steel rings (FIG. 5). This assembly is held in a rigid, easily hydrolysable cellulose jacket. After dissolution of the jacket, the ballasted strips are deployed inside the rumino-reticular sac of the animal and have for this reason, additional stability.

All of these devices as described in the foregoing, are particularly well adapted to be administered orally to an animal, to dwell in the rumino-reticular sac of the animal for a very long period during which they release the active principle—prophylactic or therapeutic—in a continuous, regular, uniform manner.

A device according to the present invention is particularly well adapted for combating internal parasites in ruminants (ovine, caprine or bovine cattle) particularly by the fact that the doses of prophylactic or therapeutic agent released can be calculated so as to act on the parasites in their larval stage (hence, with maximum effectiveness of the active principle) progressively according to their ingestion by the animals.

As a function of the necessary liberated doses, it is possible to adapt the concentration of the active substance in the polymeric matrix; the latter can vary from 1 to 55 percent by weight of the matrix portion. In addition, the duration of diffusion can be regulated by adjustment of several parameters, including the total diffusion surface, the concentration of active substance, the incorporation of adjuvants or additives, and the nature of the thermoplastic polymer.

EXAMPLES OF COMPOSITION

EXAMPLE 1

|  | Parts by Weight |
| --- | --- |
| Levamisole hydrochloride | 23.8 |
| Octyl adipate | 20 |
| Epoxydized soya oil | 2 |
| Calcium stearate | 0.5 |
| Lactose | 20 |
| P.V.C. homopolymer | 33.7 |

From this composition a hollow cylinder is formed by extrusion. After cutting-up, the dimensions of the extruded parts are as follows:

| length | 100 mm |
| --- | --- |
| total diameter | 24 mm |
| thickness of the wall | 10 mm |
| total weight | 52.75 g |

This plastic element is ballasted by a solid stainless steel cylinder with the following dimensions:

| length | 100 mm |
| --- | --- |
| diameter | 4 mm | which is inserted into the hole of the cylinder.

The total weight of the device is about 73 g, corresponding to a density of 1.6 g/ml. It contains 12.55 g of Levamisole hydrochloride.

EXAMPLE 2

|  | Parts by weight |
| --- | --- |
| Levamisole hydrochloride | 45 |
| Di-(ethyl 2 hexyl)adipate | 20 |
| Epoxydized soya oil | 4 |
| Calcium stearate | 2.5 |
| P.V.C. homopolymer | 28.5 |

The homogeneous powder obtained is injected hot into a mold whose dimensions enable a cylindrical system to be produced as described in FIG. 3. The metal cylinder, with the dimensions of 100 mm length and 14 mm diameter, is imprisoned in the polymeric matrix in the course of the molding operation.

The final device of 30 mm large diameter, 25 mm small diameter and 110 mm length weighs about 187 g.

Its density is 2.6 g/ml and contains 30.15 g of Levamisole hydrochloride.

EXAMPLE 3

The device as described in Example 2 is covered over half its length with a fine film P of silicone elastomer cross-linkable at normal temperature of 5/10 mm thickness (FIG. 3a).

EXAMPLE 4

|  | Parts by Weight |
| --- | --- |
| Morantel tartrate | 40 |
| Di-octyl phthalate | 20 |
| Calcium stearate | 2.5 |
| Epoxydized soya oil | 4 |
| P.V.C. homopolymer | 33.5 |

The device is produced in accordance with the procedure described in Example 2. It weighs about 195 g and contains 25.5 g of Morantel tartrate. Its density is in the vicinity of 2.6 g/ml.

EXAMPLE 5

|  | Parts by Weight |
| --- | --- |
| Pyrantel tartrate | 40 |
| Octyl adipate | 25 |
| Calcium stearate | 2 |
| Epoxydized soya oil | 0.5 |
| P.V.C. homopolymer | 32.5 |

The powder obtained is heated in a mold whose dimensions enable an oblong system to be obtained 100 mm long and 30 mm maxium diameter.

This system has a cylindrical central cavity open at one end enabling the insertion of a stainless steel metal cylinder 80 mm long and 8 mm in diameter.

The final device thus forms a bolus administered as such to ruminants.

It weighs about 105 g, its density is 2.1 g/ml and it contains 20.5 g of Pyrantel tartrate.

EXAMPLE 6

|  | Parts by Weight |
| --- | --- |
| Fenbendazole | 30 |
| Ethyl-2 hexyl adipate | 20 |
| Lactose | 15 |
| Calcium stearate | 2 |
| Epoxidized soya oil | 0.5 |
| P.V.C. homopolymer | 32.5 |

The homogeneous powder obtained is heated in a mold identical with that described in Example 2. The device, with identical physical characteristics to those of the device of Example 2, contains 20.1 g of fenbendazole.

EXAMPLE 7

|  | Parts by Weight |
| --- | --- |
| Ivermectine | 3.5 |
| Ethyl-2 hexyl adipate | 25 |
| Lactose | 15 |
| Calcium stearate | 2.5 |
| Epoxidized soya oil | 15 |
| P.V.C. homopolymer | 0.5 |
| P.V.C homopolymer | 38.5 |

By extrusion, a hollow cylinder is formed from the homogeneous powder having the composition indicated.

After being cut up, the dimensions are as follows:

|  |  |
| --- | --- |
| Length | 30 mm |
| Total diameter | 24 mm |
| Wall thickness | 5 mm |
| Total weight | 10.7 g |

This plastics elements is weighted by a solid cylinder of stainless steel 14 mm in diameter and 30 mm in length which is inserted into the base of the cylinder.

The total weight of the device is about 46.5 g having a density of 3.4 g/ml. It contains 0.375 g of Ivermectine.

REPORTS OF TESTS OF RELEASE IN VITRO

EXAMPLE 8

1. Experimental procedure:

The device to be tested is immersed in a liter of drinkable water adjusted to pH 7 and thermostated to 37° C.

The container is equipped with a mechanical dipping stirring system (anchor or helix type) driven with a slow rotary motion (100 rpm) ensuring the homogeneity of the solution.

The whole of the assembly is placed in darkness.

Daily samples of 1 ml of solution are taken and the whole of the volume of liquid is replaced by drinkable water.

The concentration of active principle, released daily, is determined by the technique of high-performance liquid chromatography.

2. Results

The kinetics of elimination in vitro of the active principle is determined on the device described in Example 1.

Analysis by high-performance liquid chromatography gives the results indicated in Table I below:

TABLE I

The amounts of Levamisole hydrochloride released are expressed in percent of the initial dose and are cumulated

| Days in vitro | % Leyamisole Hydrochloride released |
| --- | --- |
| 3 | 6.3 |
| 5 | 18.1 |
| 7 | 24.7 |
| 10 | 38.3 |
| 15 | 44.9 |
| 18 | 50.1 |
| 20 | 60.9 |
| 25 | 70.1 |
| 30 | 75.5 |
| 40 | 87.6 |
| 50 | 95.9 |

After 50 days, the device is taken up from the bath and the amount remaining of Levamisole hydrochloride contained in the plastics weft is analyzed. The results obtained are of the order of 4.1% and confirm the total eliminated values.

EXAMPLE 9

1. Experimental procedure:

It is identical with that of Example 8.

2. Results:

The kinetics of elimination in vitro of the active principle is determined on the device described in Example 2.

Analysis, by high-performance liquid chromatography, gives the results indicated in Table II below:

TABLE II

The amounts of Levamisole hydrochloride released are expressed in percent of the initial dose and are cumulated

| Days | % Levamisole HCl | Days | % Levamisole HCl |
| --- | --- | --- | --- |
| 3 | 6.8 | 50 | 42.4 |
| 6 | 9.4 | 57 | 47.5 |
| 10 | 12.8 | 65 | 54.2 |
| 15 | 17.4 | 74 | 61.6 |
| 20 | 22.2 | 80 | 66.6 |
| 27 | 28.0 | 92 | 76.6 |
| 34 | 33.7 | 98 | 81.6 |
| 37 | 35.5 | 105 | 87.4 |
| 43 | 39.0 | 110 | 91.6 |
|  |  | 115 | 95.7 |

After 115 days, the device was taken up from the bath and the remaining amount of Levamisole hydrochloride contained in the plastics weft is analyzed.

The results obtained were of the order of 3.5% and confirmed the eliminated cumulated values.

EXAMPLE 10

1. Experimental protocol:

It was identical with that of Example 8.

2. Results:

The kinetics of the elimination in vitro of the active principle was determined on the device described in Example 3.

Analysis by high-performance liquid chromatography gave the results indicated in Table III below:

TABLE III

The amounts of Levamisole hydrochloride released are expressed in percent of the initial dose and are cumulated

| Days | % Levamisole HCl | Days | % Levamisole HCl |
|------|------------------|------|------------------|
| 3    | 4.7              | 98   | 45.3             |
| 6    | 5.8              | 109  | 50.3             |
| 10   | 8.3              | 115  | 53.0             |
| 15   | 10.6             | 125  | 57.5             |
| 20   | 14               | 140  | 64.7             |
| 27   | 17.1             | 165  | 75.8             |
| 34   | 19.6             | 180  | 82.5             |
| 37   | 20.5             | 195  | 89.3             |
| 43   | 22.6             | 210  | 96.2             |
| 50   | 23.4             |      |                  |
| 57   | 26.6             |      |                  |
| 65   | 30.28            |      |                  |
| 87   | 40.3             |      |                  |

After 210 days the device was taken up from the bath and the remaining amount of Levamisole hydrochloride contained in the plastic weft.

The results obtained were of the order of 4.5% and confirmed the eliminated cumulated values.

In addition, it emerges from a comparison of the values of the Table II and III that the amounts eliminated by the device of Example 3 are a half less than those of the device of Example 2.

REPORT OF TESTS OF RELEASE IN VIVO

EXAMPLE 11

For practicing a process according to the invention, i.e. the treatment of ruminants by means of a device as described above, there was determined the speed of release of the active principle (mg/day) using cylindrical devices whose composition is indicated in the Example 2.

These devices were administered to twelve young calves having a ruminal fistula.

The devices were withdrawn 15, 30, 45, 60, 75, 95 days after, in order to evaluate the remaining amount of active principle.

Each of the results indicated in Table IV is an average of two values:

TABLE IV

| Days | animal n° | Levamisole HCl mg/day |
|------|-----------|-----------------------|
| 15   | 1         | 290                   |
|      | 2         | 260                   |
| 30   | 3         | 280                   |
|      | 4         | 260                   |
| 45   | 5         | 250                   |
|      | 6         | 245                   |
| 60   | 7         | 205                   |
|      | 8         | 240                   |
| 75   | 9         | 265                   |
|      | 10        | 250                   |
| 95   | 11        | 225                   |
|      | 12        | 258                   |

Namely an average of 252.33 in 95 days.

EXAMPLE 12

Experiments carried out under rearing conditions and relating to 40 bovine cattle weighing on the average 400 kg.

The animals were divided into four batches of 10: Batch A, Batch B, Batch C and Batch D.

The pasture not having undergone any disinfection was divided into four separate equal enclosures, sufficiently large for each to receive 10 animals during the whole pastural system.

The experiments started the 1st of May to end on the 24th August.

Batch A was constituted by untreated animals.

Batch B underwent two treatments in time: 35 days and 56 days with a single oral dose of 10 mg/kg body weight of Levamisole.

Batches C and D were constituted by animals receiving the device of Example 2, which corresponds to a daily dose of 220 mg of Levamisole base during 115 days.

Coproscopic checks were carried out for all of the four batches at times: D 0, D 34, D 37, D 55 and D 58.

The animals of Batches A, B and C were autopsied on day D 116.

The animals of Batch D were autopsied at day D 137.

The examination consisted of counting adult gastro-intestinal nematodes or those in larval form present in the lumen of the digestive tract.

The percentage reduction is calculated by:

$$R\% = \frac{\text{Total number of control worms} - \text{Total number of treated worms}}{\text{total number of control worms}} \times 100$$

The experiment can be summarized in Table V below:

TABLE V

| Days | Actions | Batch A | Batch B | Batch C | Batch D |
|------|---------|---------|---------|---------|---------|
| 0    | Coproscopy | Negative | Negative | Negative Device | Negative |
| 1    | Treatment | — | — | | Device |
| 3    | Putting to Pasture | Yes | Yes | Yes | Yes |
|      | Coproscopy | Positive | Positive | Negative | Negative |
| 35   | Treatment | — | Levamisole 10 mg/kg | — | — |
| 37   | Coproscopy | Negative | Negative | Negative | Negative |
| 55   | Coproscopy | Very Positive | Positive | Negative | Negative |
| 56   | Treatment | — | Levamisole 10 mg/kg | — | — |
| 58   | Coproscopy | Negative | Negative | Negative | Negative |
| 116  | Autopsy and R % | Massive Infestation R = 0% | Average Infestation R = 60% | Infestation Nil R = 98% | — |
| 137  | Autopsy and R % | — | — | — | Infestation Practically Nil R = 95% |

The results of these experiments show that the use of the device according to the present invention enables animals to be protected from any infestation throughout the pastural season.

On the contrary, the animals of Batch B, treated periodically, show a momentary parasite elimination after each treatment, followed by a massive re-infestation some days later.

The animals of Batch D, slaughtered three weeks after the arrest of the release of Levamisole by the device had practically nil infestation.

This demonstrates the destruction of the helminth's larvae present initially in the pasture.

The device, as described in Example 2, hence permits effective protection for four months against gastrointestinal parasites for large beef cattle.

EXAMPLE 13

The experiments were carried out under rearing conditions and related to three batches of six beef cattle weighing on the average 150 kg.

The diagram of the test was identical with that described in Example 12.

Batch A was constituted by untreated animals.

Batch B was constituted by animals undergoing three treatments based on a single oral dose of Levamisole, at 10 mg per kg of body weight.

Batch C was constituted by animals receiving the device described in Example 3.

All of the actions are summarized in Table VI below:

TABLE VI

| DAYS | ACTIONS | BATCH A | BATCH B | BATCH C |
|---|---|---|---|---|
| 0 | coproscopy | negative | negative | negative |
| 1 | treatment | 0 | 0 | |
| 4 | putting to pasture | yes | yes | yes |
| 40 | coproscopy | positive | positive | negative |
| 42 | treatment | 0 | Levamisole 10 mg/kg | 0 |
| 44 | coproscopy | positive | negative | negative |
| 71 | coproscopy | very positive | | negative |
| 73 | treatment | 0 | Levamisole 10 mg/kg | 0 |
| 75 | coproscopy | very positive | negative | negative |
| 108 | coproscopy | positive | positive | negative |
| 110 | treatment | 0 | Levamisole 10 mg/kg | 0 |
| 112 | coproscopy | very positive | negative | negative |
| 145 | coproscopy and R % | massive infestation R = 0% | average infestation av R = 60% | infestation nil R = 98% |

It emerges from this table that the device of Example 3, which corresponds to a daily dose of 120 to 170 mg of Levamisole base during 150 to 200 days, permits very effective protection against helminths.

Thus as emerges from the foregoing, the invention is in no way limited to those of its types of its applications and embodiments which have just been described more explicitly; it encompasses, on the contrary, all modifications which may come to the spirit of the technician in the art, without departing from the scope, nor the range of the present invention.

We claim:

1. A device for enabling release at regulated speed into a liquid medium of one or more substances active in veterinary medicine, said device being constituted by an insoluble macro-molecular and thermoplastic solid polymeric matrix support based on insoluble polymer or copolymer comprising adjuvant and additive, enabling the progressive and programmed release of said one or more incorporated active substances, wherein the initial concentration of said one or more active substances on the one hand and the surface of the insoluble polymeric matrix support through which the diffusion is effected on the other hand are determined as a function of the duration of release and the desired daily released amount, said matrix support totally or almost totally enclosing one or more masses of dense material conferring to the whole device a density higher than 1.3 g/ml, said matrix support retaining its surface during use of the device.

2. A device according to claim 1, having a cylindrical or oblong shape.

3. A device according to claim 1, wherein the speed of diffusion of the one or more active substances is regulated by an external film extending on part of the matrix support and formed by means of an impermeable substance as cross-linkable silicone elastomers or epoxy.

4. A device according to any one of claims 1 to 3, wherein said matrix support is an extruded or hot molded support of the polymer or copolymer of chemical substances taken from the group which comprises vinyl polymers, polyethylenes, polypropylenes, polyacetates and polyurethanes.

5. A device according to any one of claims 1 to 3, wherein the dense material is a mineral or metal.

6. A device according to any one of claims 1 to 3, wherein the liquid medium is at a site in the organism of an animal.

7. A device according to claim 6, wherein the site selected in the organism of an animal is the ruminoreticular sac of a ruminant.

8. A device according to claim 1 or 2 wherein the active substance designed to be released in regulated and continuous manner, over a long period, is selected among substances with therapeutical or prophylactic activity for ruminant the device having a density higher than 2 g/ml so as to be retainable within the ruminoreticular sac of said ruminant.

9. A device according to claim 8, wherein the substance with prophylactic or therapeutic activity is an antihelmintic agent taken from the group which comprises Levamisole, Tetramisole, Morantel, Pyrantel, Nitroxynil and their soluble salts, Albendazole, Oxybendazole, Oxfendazole, Mebendazole and Ivermectine.

10. Method of treating ruminant with a device according to any one of claims 1 to 3, comprising administering said device to the ruminant in the form of a bolus, the regurgitation of which is prevented, so that all or almost all of the active substance is absorbed according to a predetermined time program.

11. A device according to claim 3 wherein the impermeable substance is a cross-linkable silicone elastomer.

12. A device according to claim 3 wherein the impermeable substance is an epoxy resin.

13. A device of claim 1 wherein the polymer or copolymer comprises vinyl polymer.

14. A device of claim 1 wherein the polymer comprises polyethylene.

15. A device of claim 1 wherein the polymer comprises polypropylene.

16. A device of claim 1 wherein the polymer or copolymer comprises polyacetate.

17. A device of claim 1 wherein the polymer or copolymer comprises polyurethane.

18. A device of claim 1 wherein the polymer or copolymer comprises vinyl acetate.

19. A device for enabling release at regulated speed into a liquid medium of one or more substances active in veterinary medicine, said device being constituted by an insoluble macromolecular and thermoplastic solid matrix support based on insoluble polymer or copolymer comprising adjuvant and additive, enabling the progressive and programmed release of said one or more incorporated active substances, wherein the initial concentration of said one or more active substances on the one hand and the surface of the insoluble polymeric matrix support through which the diffusion is effected on the other hand are determined as a function of the duration of release and the desired daily released amount, said matrix support being held by at least one tip or at least one ring of dense material conferring to the whole device a density higher than 1.3 g/ml.

* * * * *